United States Patent [19]

Yoshida et al.

[11] Patent Number: 5,703,264
[45] Date of Patent: Dec. 30, 1997

[54] PROCESS FOR PRODUCING ALIPHATIC NITRILE

[75] Inventors: Wataru Yoshida; Tetsuaki Fukushima; Hideki Taniguchi; Hiroshi Abe, all of Wakayama, Japan

[73] Assignee: Kao Corporation, Tokyo, Japan

[21] Appl. No.: 670,787

[22] Filed: Jun. 24, 1996

[30] Foreign Application Priority Data

Jul. 6, 1995 [JP] Japan ................................. 7-170758

[51] Int. Cl.$^6$ ............................................. C07C 253/00
[52] U.S. Cl. ................................................. 558/316; 558/315
[58] Field of Search ................................... 558/316, 315

[56] References Cited

U.S. PATENT DOCUMENTS

| | | |
|---|---|---|
| 2,337,421 | 12/1943 | Spence et al. . |
| 2,337,422 | 12/1943 | Spence et al. . |
| 3,022,349 | 3/1962 | Lemon et al. ................ 260/585 |
| 3,491,139 | 1/1970 | Biale ............................ 260/465.9 |

FOREIGN PATENT DOCUMENTS 696652  10/1964  Canada .
60-104043  6/1985  Japan .

*Primary Examiner*—Johann Richter
*Assistant Examiner*—Ebenezer Sackey
*Attorney, Agent, or Firm*—Oblon, Spivak, McClelland, Maier & Neustadt, P. C.

[57] ABSTRACT

The process for producing an aliphatic nitrile comprising reacting an aliphatic alcohol having 6 to 40 carbon atoms with ammonia (a) in the presence of a copper/transition metal element in the fourth period other than Cr/platinum group element in the eighth group catalyst, (b) under a reaction system pressure in the range of from atmospheric pressure to 100 atm, (c) at a reaction system temperature in the range of from 100° to 250° C., (d) while introducing at least one gas selected from the group consisting of inert gases and hydrogen gas into the reaction system, (e) removing water formed by the reaction out of the reaction system, and (f) controlling the amount of the ammonia contained in the gas (exclusive of the water formed by the reaction) discharged out of the reaction system to 5 to 50% by volume based on the volume of the gas discharged (exclusive of the water formed by the reaction) makes it possible to produce various kinds of aliphatic nitriles.

7 Claims, No Drawings

PROCESS FOR PRODUCING ALIPHATIC NITRILE

FIELD OF THE INVENTION

The present invention relates to a process in which an aliphatic alcohol is reacted with ammonia to produce a nitrile corresponding to the above alcohol.

DISCUSSION OF THE BACKGROUND

Nitriles are industrially important materials as intermediates for producing primary amines having wide uses. Examples of materials which can be directly or indirectly produced from nitriles include, in addition to the primary amines described above, secondary amines, tertiary amines and quaternary ammonium salts which are used as, e.g., surfactants and softening bases.

Processes for producing nitriles by reacting fatty acids with ammonia has so far been well known. When fatty acids are used as starting materials, resulting nitriles have chemical structures corresponding to the fatty acids used. However, because of restrictions in the kinds of fatty acids, the use of the fatty acids as starting materials provides only nitriles having specific structures. On the other hand, several processes for producing nitriles from alcohols have also been known [See U.S. Pat. Nos. 2,337,421 and 2,337,422 (published on Dec. 21, 1943, assignee: Rohm & Haas Company), and Japanese Patent Publication-A No. 60-104043 (published on Jun. 8, 1985) and U.S. Pat. No. 4,415,755 (published on Nov. 15, 1983, assignee: TEXACO INC.) corresponding thereto]. Because there are more kinds of alcohols than fatty acids, the use of alcohols as starting materials makes it possible to produce nitriles having various chemical structures. However, the publications described above disclose only processes for producing nitriles having relatively low molecular weights which have carbon atoms of up to about 8, by a gaseous phase reaction, and merely suggest that when alcohols having high boiling points, i.e., alcohols having high molecular weights or branched-chain alcohols are used as starting materials, nitriles can be produced therefrom by effecting the reaction under a reduced pressure condition.

Thus, a process for effectively producing, from an aliphatic alcohol having relatively many carbon atoms, a nitrile corresponding thereto has not been known.

SUMMARY OF THE INVENTION

Accordingly, it is one object of the present invention to provide a process for producing a nitrile using an alcohol and ammonia as starting materials, by which aliphatic nitriles having various chemical structures can be produced.

This and other objects, which will become apparent during the following detailed description, have been achieved by the inventors' discovery that the above-mentioned object can be attained when a specific catalyst is used and a specified condition is selected in reacting an alcohol with ammonia.

Thus, the present invention provides a process for producing an aliphatic nitrile comprising reacting an aliphatic alcohol having 6 to 40 carbon atoms with ammonia:

(a) in the presence of a catalyst comprising copper, a transition metal element in the fourth period other than Cr and a platinum group element in the eighth group, (b) under a reaction system pressure in the range of from atmospheric pressure to 100 atm, (c) at a reaction system temperature in the range of from 100° to 250° C., (d) while introducing at least one gas selected from the group consisting of inert gases and hydrogen gas into the reaction system, (e) removing water formed by the reaction out of the reaction system, and (f) controlling the amount of the ammonia contained in the gas (exclusive of the water formed by the reaction) discharged out of the reaction system to 5 to 50% by volume based on the volume of the gas discharged (exclusive of the water formed by the reaction).

According to the process of the present invention, nitriles having chemical structures corresponding to those of starting alcohols are produced.

The present invention includes a process for producing an alkylnitrile, characterized by reacting a higher alcohol with ammonia under conditions satisfying all the following items (a) to (e): conditions (a) the reaction is carried out in the presence of a copper-fourth period transition metal element (exclusive of Cr)-eighth group platinum group element catalyst, (b) the reaction is carried out by controlling the reaction system comprising the higher alcohol and the ammonia to a pressure of from atmospheric to 100 atm, (c) the reaction is carried out by controlling the reaction system to a temperature of from 100° to 250° C., (d) the reaction is carried out while introducing an inert gas, hydrogen gas or a mixture thereof into the reaction system, and removing water formed by the reaction out of the reaction system, and (e) the reaction is carried out while controlling the amount of the ammonia contained in the gas (hereinafter referred to as exhaust gas) discharged out of the reaction system, exclusive of the formed water, to 5 to 50% by volume (based on the exhaust gas).

The catalyst according to the present invention preferably contains metals in a weight ratio of copper:the transition metal element in the fourth period other than Cr:the platinum group element in the eighth group of 0.1 to 10:1:0.001 to 0.5.

It is preferred that the transition metal element in the fourth period is at least one member selected from the group consisting of nickel, cobalt and zinc, and the platinum group element in the eighth group is at least one member selected from the group consisting of platinum, palladium and ruthenium.

Although the aliphatic alcohol according to the present invention has 6 to 40 carbon atoms, saturated and unsaturated alcohols having 8 to 36 carbon atoms are preferable, saturated and unsaturated (having a double bond and no triple bond) alcohols having 8 to 36 carbon atoms are still more preferable, and saturated alcohols having 8 to 36 carbon atoms are particularly preferable.

The gas introduced into the reaction system is preferably an inert gas.

Further scope and applicability of the present invention will become apparent from the detailed description and examples given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description and these examples.

DETAILED DESCRIPTION OF THE INVENTION

In the present invention, the selection of the species of the catalyst is most important. The catalyst components to be used in the present invention comprise copper, a transition metal element in the fourth period other than Cr and a platinum group element in the eighth group. The transition metal element in the fourth period is preferably at least one member selected from the group consisting of nickel, cobalt and zinc, particularly preferably at least one member selected from the group consisting of nickel and zinc. Cr is excluded in that Cr causes environmental pollution problems. The platinum group element in the eighth group is preferably at least one member selected from the group consisting of platinum, palladium and ruthenium, particularly preferably at least one member selected from the group consisting of palladium and ruthenium.

The catalyst of the present invention preferably contains metals in a weight ratio of copper:a transition metal element in the fourth period other than Cr:a platinum group element in the eighth group of 0.1 to 10:1:0.001 to 0.5, and particularly preferably contains these metals in a weight ratio of 1 to 8:1:0.01 to 0.2. The catalyst according to the present invention containing the metal atoms in the above ratio contributes highly to an efficient production of aliphatic nitriles.

The reaction according to the present invention is suitably accelerated when the three components of copper, the transition metal element in the fourth period other than Cr and the platinum group element in the eighth group exist in the reaction system as catalyst components. That is, the three components described above are substantially essential. The catalytic effect is exhibited by the interactions between the three components described above.

The catalyst according to the present invention exhibits its catalytic activity when it is subjected to activation. The forms of the metal elements and that of the catalyst before activation are not specifically restricted as long as the desired catalytic activity is exhibited after activation, and any forms can be selected. Further, the form of the catalyst after activation and the state in the reaction system are not specifically restricted as well, as long as the desired catalytic activity is exhibited after activation.

When the reaction is effected in a gaseous phase (ammonia)/liquid phase (aliphatic alcohol) system, the above three metal elements used as the catalyst components are preferably any of:

1) the above metals as they are, the oxides or hydroxides thereof, or a mixture thereof, which have forms capable of being dispersed in a liquid phase in the reaction system, 2) a mixture of three catalysts each comprising a suitable support and any of copper, the transition metal element in the fourth period other than Cr and the platinum group element in the eighth group supported thereon, or a catalyst comprising a support and the three components of copper, the transition metal element in the fourth period other than Cr and the platinum group element in the eighth group uniformly supported thereon, which has a form capable of being dispersed in a liquid phase in the reaction system, 3) salts of an aliphatic carboxylic acid with the above-described metals, or complexes comprising suitable ligands and the above-described metals stabilized by them, which have forms capable of forming a homogeneous metal colloid when the salts or the complexes are added to a liquid phase in the reaction system, 4) a mixture of one(s) having a form capable of being dispersed in a liquid phase as described in the above item 1) or 2), and other one(s) having a form capable of being a homogeneous state as described in the above item 3), and 5) a catalyst having a form, before activation, capable of being dispersed in a liquid phase in the reaction system, and a form, after activation, capable of forming a homogeneous metal colloid.

When the reaction is effected in a gaseous phase system, the above three metal elements used as the catalyst components are preferably any of:

6) the above metals as they are, the oxides or hydroxides thereof, or a mixture thereof, which have forms capable of being fixed to a reactor, 7) a mixture of three catalysts each comprising a suitable support and any of copper, the transition metal element in the fourth period other than Cr and the platinum group element in the eighth group supported thereon, or a catalyst comprising a support and the three components of copper, the transition metal element in the fourth period other than Cr and the platinum group element in the eighth group uniformly supported thereon, which has a form capable of being fixed to a reactor, 8) salts of an aliphatic carboxylic acid with the above-described metals, or complexes comprising suitable ligands and the above-described metals stabilized by them, which have forms capable of being fixed to a reactor, and 9) a mixture of one(s) having the form described in the above item 6) or 7), and other one(s) having the form described in the above item 8).

Considering the stabilization of catalyst metals, in other words, the fixation of active sites, and the durability against catalyst poison, a still more preferable catalyst to be used in the process of the present invention is one comprising a suitable support and the above-described three components uniformly supported thereon.

When the three components of copper, the transition metal element in the fourth period other than Cr and the platinum group element in the eighth group are supported on a support, materials generally used as supports for catalysts can be used as the support. Examples of suitable supports include alumina, silica-alumina, magnesia, titania, diatomaceous earth, silica, activated carbon, and natural and synthetic zeolites, and preferably, alumina and synthetic zeolite. Although the amount of the catalyst components supported on the support can arbitrary be determined, it is usually an amount such that the total amount of metal atoms is 10 to 150% by weight, preferably 30 to 100% by weight based on the weight of the support, regardless of the chemical structures of the catalyst components.

The method by which the three metal components described above are supported on a support may suitably be selected from among various methods. The metals which are supported and which are raw materials of the catalyst are preferably in the form of oxides, hydroxides or salts thereof. There can be used, for example, chlorides, sulfates, nitrates, acetates and aliphatic carboxylic acid salts of the metals described above, and complexes of the metals described above, such as acetylacetone complexes and dimethylglyoxime complexes thereof. Further, in the case of the platinum group element in the eighth group, a carbonyl complex, amine complex or phosphine complex of the element can also be used.

Examples of methods by which the metal components having the above-described forms are supported on a support include a method comprising immersing a support in a solution of salts of the above-described metal elements to sufficiently impregnate the support with the solution and drying and burning the resulting support, another method comprising sufficiently mixing a support with an aqueous solution of salts of the above-described metal elements, and adding a basic aqueous solution such as aqueous solutions of sodium carbonate and sodium hydroxide and aqueous ammonia to the resulting mixture to precipitate the salts of the above-described metal elements on the support, and the other method comprising simultaneously adding an aqueous solution of salts of the above-described metal elements and a basic aqueous solution such as aqueous solutions of sodium carbonate and sodium hydroxide and aqueous ammonia to a slurry of a support with water so as to adjust the pH of the slurry to a predetermined value (for example, pH 7), thereby precipitating the salts of the above-described metal elements on the support, and drying and burning the resulting support. When the aqueous solution of the salts of the above-described metal elements and the basic aqueous solution are simultaneously added to the slurry of the support with water, the aqueous solution of the salts of the metal elements and the basic aqueous solution are preferably used in such a ratio that the amount of the base such as sodium carbonate is 0.8 to 1.2 gram equivalent per gram equivalent of the total of the metal elements described above.

It may be possible that a catalyst comprising only the copper component supported on a support is prepared by the method described above, and then another catalyst comprising the component of the transition metal element in the fourth period other than Cr supported on a support and another catalyst comprising the component of the platinum group element in the eighth group supported on a support; or the other catalyst comprising the component of the transition metal element in the fourth period other than Cr and the component of the platinum group element in the eighth group supported on a support are(is) added thereto. Alternatively, it may be possible that a catalyst comprising the copper component and the component of the transition metal element in the fourth period other than Cr supported on a support is prepared by the method described above, and then the other catalyst comprising the component of the platinum group element in the eighth group supported on a support is added to the catalyst, or an aliphatic carboxylic acid salt or a complex of the platinum group element in the eighth group is added to the catalyst to thereby combine the component of the platinum group element in the eighth group with the copper component and the component of the transition metal element in the fourth period other than Cr. In the present invention, the catalyst comprising the three components uniformly supported on a support prepared by the latter method is particularly preferred.

Although the amount of the catalyst used is not specifically restricted, it is usually, based on the weight of the aliphatic alcohol, 0.1 to 10% by weight, preferably 0.2 to 2% by weight, as defined as the amount of the catalyst having a form at the use thereof, whether supported or not.

In the present invention, it is desirable to subject the catalyst to activation treatment before the reaction. Examples of such activation treatments include reductions using reducing agents such as hydrogen gas, an aqueous solution of formaldehyde, and sodium borohydride.

The alcohol used as the starting material in the present invention is an aliphatic alcohol having 6 to 40 carbon atoms, particularly a linear or branched, saturated or unsaturated monohydric alcohol having 6 to 40 carbon atoms. Among such alcohols, preferred are aliphatic alcohols having 8 to 36 carbon atoms, and more preferred are aliphatic alcohols having 12 to 28 carbon atoms. The hydrocarbon portion of such an alcohol is preferably a saturated (that is, an alkyl group) or unsaturated (having a double bond and no triple bond, that is, an alkenyl group) hydrocarbon group, more preferably a saturated hydrocarbon group.

Examples of aliphatic alcohols for use in the present invention include octyl alcohol, lauryl alcohol, myristyl alcohol, stearyl alcohol, behenyl alcohol and oleyl alcohol which are linear alcohols, and mixtures thereof, and Fine Oxocol 180 and 180N (manufactured by Nissan Chemical Co., Ltd.), Diadol 18G (manufactured by Mitsubishi Chemical Industries Co., Ltd.) and Dobanol 23-I (manufactured by Mitsubishi Yuka Co., Ltd.) which are branched alcohols.

In the present invention, it is necessary to conduct the reaction under such conditions that the pressure of the reaction system is from atmospheric pressure to 100 atm, preferably from atmospheric pressure to 20 atm, and that the temperature of the reaction system is from 100° to 250° C., preferably from 200° to 250° C. When either the pressure or the temperature or both of them is(are) out of the range(s) described above, it is difficult to sufficiently achieve the object of the present invention.

Here, the "reaction system" comprises a catalyst(s), an aliphatic alcohol and ammonia as the starting materials, and an inert gas, hydrogen gas, or a mixture thereof which will be described below. The reaction system is a gaseous phase/liquid phase system, a gaseous phase/solid phase system or a gaseous phase/liquid phase/solid phase system. The liquid phase may contain a solvent which is inert to the reaction.

In the present invention, the reaction is conducted while introducing an inert gas, hydrogen gas, or a mixture thereof into the reaction system together with ammonia gas and removing water formed by the reaction out of the reaction system. Among inert gases, hydrogen gas and mixtures thereof, inert gases are particularly preferred. Examples of the inert gases to be used in the present invention include nitrogen, helium and argon, and any one may be used. Usually, the gaseous phase in the reaction system is turned into an atmosphere of an inert gas, hydrogen gas or a mixed gas thereof, then the reaction system is heated while introducing the inert gas, the hydrogen gas or the mixed gas thereof into the reaction system, and when the temperature of the system reaches the reaction temperature, ammonia gas is introduced into the reaction system.

Usually, a catalyst which has been activated by reducing with hydrogen gas is used. However, it may be possible that a catalyst which has not been activated is used, and that the catalyst is put into the reactor together with the aliphatic alcohol as the starting material, and prior to the starting of the reaction (i.e., the introduction of ammonia gas), the temperature of the reaction system is elevated up to the reducing temperature of the catalyst while introducing hydrogen gas into the reactor (the reaction system), thereby reducing the catalyst. After the completion of the reduction of the catalyst, an inert gas, hydrogen gas, or a mixture thereof is introduced into the reaction system until the temperature of the reaction system reaches the reaction temperature, and the introduction of ammonia gas into the reaction system is started as usual after the reaction temperature has been reached.

The amount of the inert gas, the hydrogen gas, or the mixture thereof which is introduced into the reaction system is 1 to 100 l/hr, more preferably 10 to 50 l/hr, per kg of the aliphatic alcohol as the starting material.

Water formed by the reaction may be removed out of the reaction system either intermittently or continuously.

The ammonia gas is introduced into the reaction system in such an amount that the amount of the ammonia contained in the gas (exclusive of the water formed by the reaction) discharged out of the reaction system is usually 5 to 50% by volume, preferably 10 to 30% by volume, based on the volume of the gas (exclusive of the water formed by the reaction) discharged. The object of the present invention is achieved by introducing the ammonia gas into the reaction system in such an amount (or rate). The ammonia contained in the gas discharged is quantatively determined by, for example, gas chromatography.

Next, one preferred embodiment of the present invention will be illustrated.

An aliphatic alcohol as a starting material, and a catalyst are fed into a reactor equipped with a tube for introducing hydrogen or nitrogen, and ammonia into the reactor and a rectifying column. Although the catalyst may be fed thereinto in an arbitrary amount, the amount thereof is usually from 0.1 to 10% by weight based on the weight of the alcohol fed.

When the catalyst is reduced in the reaction system, the reaction system is heated up to the reducing temperature of the catalyst while introducing hydrogen into the reaction system at a rate of 1 to 100 l/hr, preferably 5 to 100 l/h, per kg of the alcohol after substituting nitrogen gas for the air in the reaction system. The reducing temperature is usually from 160° to 250° C. For reducing the catalyst, the reaction system is maintained at a temperature in this range for 0.5 to 3 hours.

After the completion of the reduction of the catalyst, the reaction system is set up at the predetermined reaction temperature and at the predetermined reaction pressure. The reaction temperature is from 100° to 250° C., and the reaction pressure is from atmospheric pressure to 100 atm. Thereafter, nitrogen is introduced into the reaction system. The nitrogen is introduced thereinto in an amount of 1 to 100 l/h, per kg of the aliphatic alcohol.

Next, ammonia gas is introduced into the reaction system to start the reaction. The ammonia gas is introduced in such an amount that the amount of the ammonia contained in the gas (exclusive of the water formed by the reaction) discharged is from 5 to 50% by volume, preferably from 10 to 40% by volume, and still more preferably from 10 to 30% by volume based on the volume of the gas (exclusive of the water formed by the reaction) discharged. The ammonia contained in the gas discharged is quantitatively determined by gas chromatography. The reaction is traced with gas chromatography, and the reaction is completed when the amount of the starting alcohol present in the reaction system is usually 5% or less, and preferably 1% or less, based on the amount thereof fed. After the completion of the reaction, the catalyst is removed by filtration, and the filtrate is purified by distillation. Thus, the intended aliphatic nitrile is obtained. The identification of the nitrile produced is carried out by comparing the properties thereof with those of the same substance separately synthesized.

Other characteristics of the present invention will be obvious in a series of the following descriptions regarding typical examples which are given in order to explain the present invention and do not intend to restrict the present invention.

EXAMPLES

First, the methods for preparing the catalysts used in the Examples will be shown below all together.

<Preparation of the Catalysts>

A copper-nickel-palladium supported catalyst (Catalyst A), a copper-nickel-ruthenium supported catalyst (Catalyst B), a copper-zinc-platinum supported catalyst (Catalyst C), a copper-zinc-ruthenium supported catalyst (Catalysts D and G), a copper-cobalt-palladium supported catalyst (Catalyst E), and a copper-cobalt-platinum supported catalyst (Catalyst F) were prepared in the following manner.

(1) Catalyst A

Alumina was fed into a 1-1 flask. Then, copper nitrate, nickel nitrate and palladium chloride were weighed in such a ratio that the weight ratio of the metal atoms, that is, Cu:Ni:Pd, was 2:1:0.1. They were dissolved in water and the resulting aqueous solution was fed into the flask described above. The mixture of the alumina and the aqueous solution thus obtained was heated while stirring. When the temperature reached 90° C., a 10% $Na_2CO_3$ aqueous solution was gradually dropwise added to this mixture. The 10% $Na_2CO_3$ aqueous solution was used in such an amount that the amount of sodium carbonate was one gram equivalent per gram equivalent of the total amount of copper nitrate, nickel nitrate and palladium chloride. After the completion of the dropwise addition, the mixture was maintained (that is, aged) at 90° C. for one hour and then filtrated. The resulting precipitate was washed with water and dried at 100° C. for 10 hours, followed by burning at 400° C. for 3 hours. Thus, a catalyst comprising metal oxides supported on the alumina was obtained. The amount of the metal oxides supported, as defined as the total amount of the metal atoms in the metal oxides, was 20% by weight based on the weight of the support (i.e., the alumina).

(2) Catalyst B

Synthetic zeolite was fed into a 1-1 flask. Then, copper nitrate, nickel nitrate and ruthenium chloride were weighed in such a ratio that the weight ratio of the metal atoms, that is, Cu:Ni:Ru, was 4:1:0.01. They were dissolved in water and the resulting aqueous solution was fed into the flask described above. The mixture of the synthetic zeolite and the aqueous solution thus obtained was heated while stirring. When the temperature reached 90° C., a 10% $Na_2CO_3$ aqueous solution was gradually dropwise added to this mixture. The 10% $Na_2CO_3$ aqueous solution was used in such an amount that the amount of sodium carbonate was one gram equivalent per gram equivalent of the total amount of copper nitrate, nickel nitrate and ruthenium chloride. After the completion of the dropwise addition, the mixture was maintained (that is, aged) at 90° C. for one hour and then filtrated. The resulting precipitate was washed with water and dried at 100° C. for 8 hours, followed by burning at 600° C. for one hour. Thus, a catalyst comprising metal oxides supported on the synthetic zeolite was obtained. The amount of the metal oxides supported, as defined as the total amount of the metal atoms in the metal oxides, was 50% by weight based on the weight of the support (i.e., the synthetic zeolite).

(3) Catalyst C

Alumina was fed into a 1-1 flask. Then, copper nitrate, zinc nitrate and platinum chloride were weighed in such a ratio that the weight ratio of the metal atoms, that is, Cu:Zn:Pt, was 8:1:0.001. They were dissolved in water and the resulting aqueous solution was fed into the flask described above. The resulting mixture of the alumina and the aqueous solution was heated up to 90° C. under a reduced pressure while stirring to evaporate water. Then, the alumina contained in the flask was burned at 400° C. for 3 hours. Thus, a catalyst comprising metal oxides supported on the alumina was obtained. The amount of the metal oxides supported, as defined as the total amount of the metal atoms in the metal oxides, was 20% by weight based on the weight of the support (i.e., the alumina).

(4) Catalyst D

Synthetic zeolite was fed into a 1-1 flask. Then, copper nitrate, zinc nitrate and ruthenium chloride were weighed in such a ratio that the weight ratio of the metal atoms, that is, Cu:Zn:Ru, was 4:1:0.01. They were dissolved in water and the resulting aqueous solution was fed into the flask described above. The mixture of the synthetic zeolite and the aqueous solution thus obtained was heated while stirring. When the temperature reached 90° C., a 10% $Na_2CO_3$ aqueous solution was gradually dropwise added to this mixture. The 10% $Na_2CO_3$ aqueous solution was used in such an amount that the amount of sodium carbonate was one gram equivalent per gram equivalent of the total amount of copper nitrate, zinc nitrate and ruthenium chloride. After the completion of the dropwise addition, the mixture was maintained (that is, aged) at 90° C. for one hour and then filtrated. The resulting precipitate was washed with water and dried at 100° C. for 8 hours, followed by burning at 600° C. for one hour. Thus, a catalyst comprising metal oxides supported on the synthetic zeolite was obtained. The amount of the metal oxides supported, as defined as the total amount of the metal atoms in the metal oxides, was 50% by weight based on the weight of the support (i.e., the synthetic zeolite).

(5) Catalyst E

Synthetic zeolite was fed into a 1-l flask. Then, copper nitrate, cobalt nitrate and palladium chloride were weighed in such a ratio that the weight ratio of the metal atoms, that is, Cu:Co:Pd, was 2:1:0.1. They were dissolved in water and the resulting aqueous solution was fed into the flask described above. The mixture of the synthetic zeolite and the aqueous solution thus obtained was heated up to 90° C. under a reduced pressure while stirring to evaporate water. Then, the synthetic zeolite contained in the flask was burned at 400° C. for 3 hours. Thus, a catalyst comprising metal oxides supported on the synthetic zeolite was obtained. The amount of the metal oxides supported, as defined as the total amount of the metal atoms in the metal oxides, was 20% by weight based on the weight of the support (i.e., the synthetic zeolite).

(6) Catalyst F

Synthetic zeolite was fed into a 1-l flask. Then, copper nitrate, cobalt nitrate and platinum chloride were weighed in such a ratio that the weight ratio of the metal atoms, that is, Cu:Co:Pt, was 9:1:0.01. They were dissolved in water and the resulting aqueous solution was fed into the flask described above. The mixture of the synthetic zeolite and the aqueous solution thus obtained was heated up to 90° C. under a reduced pressure while stirring to evaporate water. Then, the synthetic zeolite contained in the flask was burned at 400° C. for 3 hours. Thus, a catalyst comprising metal oxides supported on the synthetic zeolite was obtained. The amount of the metal oxides supported, as defined as the total amount of the metal atoms in the metal oxides, was 20% by weight based on the weight of the support (i.e., the synthetic zeolite).

(7) Catalyst G

The same manner as that of the preparation of catalyst D was repeated except that the amount of the synthetic zeolite fed was a half of the amount thereof in the preparation of catalyst D. Thus, a catalyst comprising metal oxides supported on the synthetic zeolite was obtained. The amount of the metal oxides supported, as defined as the total amount of the metal atoms in the metal oxides, was 100% by weight based on the weight of the support (i.e., the synthetic zeolite).

Example 1

1200 g of stearyl alcohol (Kalcol 80, manufactured by Kao Corp.) and 6 g (0.5% by weight based on the weight of the starting alcohol) of catalyst A were fed into a 2-l separable flask. While stirring the resulting mixture, nitrogen was substituted for the air in the system, and then the temperature of the reaction system started to elevate. When the temperature reached 100° C., hydrogen gas started to blow into the system. The flow rate thereof was controlled to 40 l/h with a flow meter. Heating was further continued to elevate the temperature of the system up to 240° C., which was the reaction temperature. The gas to be introduced thereinto was changed from hydrogen gas to nitrogen gas at this temperature. The flow rate of the nitrogen gas was controlled to 40 l/hour with a flow meter. Then, ammonia gas was introduced into the system to start the reaction while controlling the introducing amount thereof so that the amount of ammonia contained in the gas discharged from the system was 20% by volume. The reaction was carried out under a normal pressure until the residual amount of the starting alcohol was 1% by weight or less based on the amount thereof fed. Thus, the intended stearonitrile was obtained at a yield of 59%.

The residual amount of the alcohol and the composition of the components contained in the reaction mixture at the termination of the reaction were analyzed with gas chromatography. The chemical structure of the intended product was identified by comparing with the standard product which was separately synthesized.

Examples 2 to 7

Nitriles were synthesized in the same manner as that in Example 1, except that Fine Oxocol 180N having the following chemical structure, manufactured by Nissan Chemical Ind. Co., Ltd., was used as the starting alcohol, and that the reaction was carried out using the catalysts shown in Table 1 at the temperatures shown in Table 1:

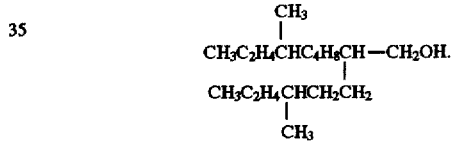

The results thereof are shown in Table 1.

Examples 8 to 10

Nitriles were synthesized in the same manner as that in Example 1, except that Diadol 18G manufactured by Mitsubishi Chemicals Industries Co., Ltd., Kalcol 20 manufactured by Kao Corp. and Dobanol 23-I manufactured by Mitsubishi Chemical Co., Ltd. each having the following chemical structure were respectively used as the starting alcohols, that catalyst D was used in place of catalyst A and that the amounts of ammonia contained in the gas discharged from the reaction system were controlled to the values shown in Table 2:

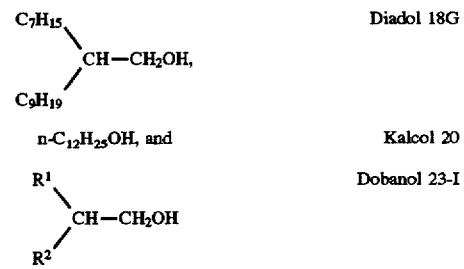

(wherein $R^1$ represents an alkyl group having 1 to 5 carbon atoms and $R^2$ represents an alkyl group having 5 to 10 carbon atoms, provided that the total of the carbon atoms of $R^1$ and $R^2$ is 10 or 11).

The results thereof are shown in Table 2.

Example 11

A nitrile was synthesized in the same manner as that in Example 8, except that hydrogen gas was used in place of nitrogen gas as the gas introduced during the reaction. The result thereof is shown in Table 2.

Example 12

A nitrile was synthesized in the same manner as that in Example 8, except that Anjecol 70N (oleyl alcohol) manufactured by Sin Nippon Rika Co., Ltd. was used as the starting alcohol. The result thereof is shown in Table 2. The compositions of the starting alcohol and the nitrile as the reaction product were analyzed by gas chromatography to find that the ratio of the amount of an unsaturated alcohol(s) contained in the starting alcohol to the amount of the starting alcohol was 68% and the ratio of the amount of an unsaturated nitrile(s) contained in the nitrile to the amount of the nitrile was 67%.

Example 13

300 g of Fine Oxocol 180N and 1.5 g (0.5% by weight based on the weight of the starting alcohol) of catalyst D were fed into a 1-l autoclave. While stirring the resulting mixture, nitrogen was substituted for the air in the system, and then the temperature of the reaction system started to elevate. When the temperature reached 100° C., hydrogen gas started to blow into the system. The flow rate thereof was controlled to 40 l/h with a flow meter. Heating was further continued to elevate the temperature of the system up to 240° C., which was the reaction temperature. The gas to be introduced thereinto was changed from hydrogen gas to nitrogen gas at this temperature, and then the pressure in the reaction system (in the autoclave) was controlled to 5 atm. The flow rate of the nitrogen gas was controlled to 40 l/hour in a normal pressure with a flow meter. Then, ammonia gas was introduced into the system to start the reaction while controlling the introducing amount thereof so that the amount of ammonia contained in the gas discharged from the system was 10 to 30% by volume. The reaction was carried out under 5 atm until the residual amount of the starting alcohol was 1% by weight or less based on the amount thereof fed. Thus, the intended nitrile was synthesized. The result thereof is shown in Table 2.

Example 14

A nitrile was synthesized in the same manner as that in Example 13, except that the pressure during the reaction was 20 atm. The result thereof is shown in Table 2.

Comparative Example 1

A nitrile was synthesized in the same manner as that in Example 8, except that a Cu-Cr catalyst (manufactured by Nikki Chemical Co., Ltd.) was used in place of catalyst A. The yield of the intended stearonitrile was 21%.

Comparative Example 2

A nitrile was synthesized in the same manner as that in Example 2, except that the amount of ammonia introduced into the reaction system was fixed (flow amount: 20 l/h) from the initiation of the reaction to the termination thereof. The amount of the ammonia contained in the gas discharged from the reaction system was 0% by volume in the early stage of the reaction but increased gradually as the reaction went on, and it reached 90% by volume at the termination of the reaction. The yield of the intended nitrile was 24%.

TABLE 1

| Catalyst | Reaction temperature | Amount of ammonia in gas discharged (% by volume based on amount of gas discharged) | Yield*1 of nitrile (%) (analyzed by gas chromagraphy) |
|---|---|---|---|
| Example 1 A | 240 | 20 | 59 |
| Example 2 B | 240 | 20 | 69 |
| Example 3 C | 220 | 20 | 54 |
| Example 4 D | 240 | 20 | 71 |
| Example 5 E | 220 | 30 | 49 |
| Example 6 F | 230 | 20 | 53 |
| Example 7 G | 240 | 20 | 70 |
| Comp. Example 1 Cu—Cr | 240 | 20 | 21 |
| Comp. Example 2 B | 240 | 0→90 | 24 |

*1: The yield does not reach 100% due to the by-productions of N,N-di(long-chain alkyl)amine and N,N,N-tri(long-chain alkyl)-amine.

TABLE 2

| Starting alcohol | Amount of ammonia in gas discharged (% by volume based on amount of gas discharged) | Yield*1 of nitrile (%) (analyzed by gas chromagraphy) |
|---|---|---|
| Example 8 Diadol 18G | 10 to 30 | 74 |
| Example 9 Kalol 20 | 10 to 30 | 65 |
| Example 10 Dobanol 23-I | 10 to 30 | 76 |
| Example 11 Diadol 18G | 10 to 30 | 45 |
| Example 12 Anjecol 70N | 10 to 30 | 62 |
| Example 13 Fine Oxocol 180N | 10 to 30 | 53 |
| Example 14 Fine Oxocol 180N | 10 to 30 | 38 |

*1: The yield does not reach 100% due to the by-productions of N,N-di(long-chain alkyl)amine and N,N,N-tri(long-chain alkyl)-amine.

Obviously, numerous modifications and variations of the present invention are possible in light of the above teachings. It is therefore to be understood that, within the scope of the appended claims, the invention may be practiced otherwise than as specifically described herein.

What is claimed is:

1. A process for producing an aliphatic nitrile comprising reacting an aliphatic alcohol having 6 to 40 carbon atoms with ammonia:

(a) in the presence of a catalyst comprising copper, a transition metal element in the fourth period other than Cr and a platinum group element in the eighth group, (b) under a reaction system pressure in the range of from atmospheric pressure to 100 atm, (c) at a reaction system temperature in the range of from 100° to 250° C., (d) while introducing at least one gas selected from the group consisting of inert gases and hydrogen gas into the reaction system, (e) removing water formed by the reaction out of the reaction system, and (f) controlling the amount of the ammonia contained in the gas, exclusive of the water formed by the reaction, discharged out of the reaction system to 5 to 50% by volume based on the volume of the gas discharged, exclusive of the water formed by the reaction.

2. The process for producing an aliphatic nitrile according to claim 1, wherein the catalyst comprising copper, a transition metal element in the fourth period other than Cr and a platinum group element in the eighth group, contains metals in a weight ratio of copper:the transition metal element in the fourth period other than Cr:the platinum group element in the eighth group of 0.1 to 10:1:0.001 to 0.5.

3. The process for producing an aliphatic nitrile according to claim 1, wherein the transition metal element in the fourth period is at least one member selected from the group consisting of nickel, cobalt and zinc, and the platinum group element in the eighth group is at least one member selected from the group consisting of platinum, palladium and ruthenium.

4. The process for producing an aliphatic nitrile according to claim 1, wherein the aliphatic alcohol has 8 to 36 carbon atoms.

5. The process for producing an aliphatic nitrile according to claim 4, wherein the aliphatic alcohol is a saturated or unsaturated (having a double bond and no triple bond) alcohol having 8 to 36 carbon atoms.

6. The process for producing an aliphatic nitrile according to claim 4, wherein the aliphatic alcohol is a saturated alcohol having 8 to 36 carbon atoms.

7. The process for producing an aliphatic nitrile according to claim 1, wherein the gas introduced into the reaction system is an inert gas.

* * * * *